(12) United States Patent
Ahari et al.

(10) Patent No.: US 11,083,464 B1
(45) Date of Patent: Aug. 10, 2021

(54) MULTISTAGE BIOABSORBABLE PLUG SYSTEM AND METHOD OF INSERTION

(71) Applicant: Med-Genesis, LLC, Clearwater, FL (US)

(72) Inventors: Frederick Ahari, Belleair Beach, FL (US); John S. Fisher, Belleair, FL (US)

(73) Assignee: Med-Genesis, LLC, Clearwater, FL (US)

( * ) Notice: Subject to any disclaimer, the term of this patent is extended or adjusted under 35 U.S.C. 154(b) by 0 days.

(21) Appl. No.: 17/200,242

(22) Filed: Mar. 12, 2021

(51) Int. Cl.
  *A61B 17/12* (2006.01)
  *A61B 17/00* (2006.01)

(52) U.S. Cl.
  CPC .... *A61B 17/12159* (2013.01); *A61B 17/0057* (2013.01); *A61B 17/1219* (2013.01)

(58) Field of Classification Search
  CPC ............ A61B 17/0057; A61B 17/0065; A61B 17/00654; A61B 17/00659; A61B 17/12159; A61B 17/1219; A61B 2017/12004
  See application file for complete search history.

(56) References Cited

U.S. PATENT DOCUMENTS

| | | | |
|---|---|---|---|
| 6,592,608 B2 | 7/2003 | Fisher et al. |
| 6,685,727 B2 | 2/2004 | Fisher et al. |
| 6,790,185 B1 | 9/2004 | Fisher et al. |
| 7,001,410 B2 | 2/2006 | Fisher et al. |
| 7,329,414 B2 | 2/2008 | Fisher et al. |

FOREIGN PATENT DOCUMENTS

WO    2019138019 A2    7/2019

*Primary Examiner* — Melanie R Tyson
(74) *Attorney, Agent, or Firm* — Nicholas Pfeifer; Smith & Hopen, P. A.

(57) ABSTRACT

A system and method for sealing openings in a body of a patient made by a medical procedure or non-medical event. The opening may be formed in soft tissue, internal organs, or hard tissue. A coaxial needle is inserted into a patient and a coagulating agent is inserted into the patient via the coaxial needle. The coagulating agent is discharged adjacent to the opening and the coaxial needle is inserted to a surgical depth. Following the procedure, the coaxial needle is retracted to a plug discharging depth. A bioabsorbable plug in at least a partially dehydrated state is then discharged from the coaxial needle and the coaxial needle is removed. The plug resides at least partially within the opening in the organ or tissue created by the coaxial needle. The combination of the coagulating agent and the expandable plug seals the opening created by the coaxial needle.

16 Claims, 8 Drawing Sheets

MULTISTAGE BIOABSORBABLE PLUG SYSTEM AND METHOD OF INSERTION

BACKGROUND OF THE INVENTION

1. Field of the Invention

This invention relates, generally, to sealing tissue. More specifically, it relates to a multistage bioabsorbable plug system and method of insertion.

2. Brief Description of the Prior Art

Numerous medical procedures and even non-medical events can result in openings in the body that need to be sealed to stop bodily fluids and/or gaseous fluids from exiting the body. For example, sealing means for closing openings are needed to stop the flow of blood, cerebral spinal fluid, air, and other fluids. These sealing means are particularly important when it comes to stopping the flow of fluids from organs.

For exemplary purposes, consider an opening made by a biopsy needle. In a biopsy procedure, a needle adapted to collect tissue is inserted into a suspected lesion, usually multiple times. When a sufficient quantity of the lesion has been collected, the samples are taken to a lab for analysis. To perform the procedure, a coaxial needle first punctures the body/tissue and inserted so that its leading/distal end is positioned near the suspected lesion. A biopsy needle is then inserted through the coaxial needle and samples are collected.

The puncture opening made by the coaxial needle may close and heal naturally if the lesion is in soft tissue such as a breast. However, if a lesion is in the lung or any other internal organs, the puncture opening made by the coaxial needle may need to be closed quickly. In fact, air leaks ("pneumothorax") commonly occur at pulmonary tissue sites that have been biopsied or dissected during surgical resection and manipulation.

Obviously, an opening in a lung is undesirable because air can leak therefrom and cause the lung to collapse. In fact, it is estimated that pneumothorax occurs in about thirty percent (30%) of lung biopsies. Openings in other organs, such as the heart, liver, kidney, and the like are also undesirable due to excess bleeding and other related problems.

Existing bioabsorbable sealant plugs and delivery methods, such as those in U.S. Pat. Nos. 6,790,185; 7,001,410; 6,685,727; 6,592,608; and U.S. Pat. No. 7,329,414 to the same inventors proved to be beneficial in reducing pneumothorax. However, pneumothorax still occurred in about 30% of lung biopsies in which these patented plugs and methods were used. Specifically, these plugs and methods are unable to account for small tears in the lungs that sometimes occur during the initial insertion (i.e., puncturing) of a needle through the pleura in a patient's lung.

Other disclosures, such as publication WO2019138019A2 rely solely on a hydrogel and teach away from the use of blood. Specifically, said publication states that the use of blood to prevent pneumothorax has "proven ineffective and [has] not been widely adopted. [The] lack of efficacy may be as [sic] a result of the physical properties of the substances injected and the lack of control over their injected location." Accordingly, these disclosures teach away from the present invention as will be described herein. Accordingly, what is needed is an improved bioabsorbable plug system and method of use to further reduce the occurrences of pneumothorax and better seal openings in other organs and tissue.

However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved bioabsorbable plug system and method of use to further reduce the occurrences of pneumothorax and better seal openings in other organs and tissue is now met by a new, useful, and nonobvious invention.

Some embodiments of the multistage bioabsorbable plug system comprise a coaxial needle, a coagulating agent, and a plug. The coaxial needle has a plug discharge port and a coagulating agent discharge port. In some embodiments, the ports are the same, while in others, they are distinct ports.

In some embodiments, the coagulating agent is a fluidic solution. Moreover, the coagulating agent is biocompatible.

During use, the coagulating agent is inserted within an organ through the coaxial needle following insertion of the coaxial needle within the organ. In some embodiments, the coagulating agent includes blood from the patient. In some embodiments, the coagulating agent is 10 cc of blood.

In some embodiments, the plug is a biocompatible hydrogel and is configured to expand upon contact with an aqueous fluid. In some embodiments, the plug is configured to absorb the coagulating agent. During use, the plug is inserted at least partially into a wall of the organ in at least a partially dehydrated state via the coaxial needle. The combination of the fluidic coagulating agent and the plug seals a hole in the organ wall created by the coaxial needle when the coaxial needle is withdrawn from the organ.

The method of present invention includes sealing an organ, such as a lung/pleura, in a patient. The method may include determining a distance between a patient's skin and the pleura. A coaxial needle can then be inserted through the patient's skin. The coaxial needle has a coagulating agent discharge port through which a coagulating agent can be discharged into the patient and a plug from the plug discharge port through which the plug can be delivered.

The method further includes bringing the coaxial needle to an initial location in which the coagulating agent discharge port is 2 cm or less in distance from the pleura. While the coaxial needle is at the initial location, the coagulating agent is injected into the patient via the coaxial needle, such that the coagulating agent exits the coagulating agent discharge port. After insertion of the coagulating agent, the coaxial needle is advanced to a surgical location and a surgical procedure can be performed.

Following the surgical procedure, the coaxial needle is retracted to a plug discharging depth, wherein the plug discharging depth includes a plug discharge port within 2 cm from an internal surface of the pleura. Then the plug is discharged from the plug discharge port while retracting the coaxial needle, such that the plug resides at least partially within the pleura. The plug is comprised of a biocompatible hydrogel configured to expand upon contact with an aqueous fluid, such as bodily fluids or the coagulating agent. After the plug is inserted, the coaxial needle is withdrawn from the patient.

Some embodiments include the plug being inserted into the coaxial needle in a dehydrated state. Some embodiments include pre-hydrating the plug prior to discharging the plug from the plug discharge port.

Some embodiments further include a step of retrieving blood from the patient and using the blood as the coagulating agent. In some embodiments, the coagulating agent is 10 cc of blood. Some embodiments further include a step of injecting the coagulating agent when the coaxial needle is at the plug discharging depth.

In some embodiments, the initial location of the coaxial needle includes a portion of the coaxial needle having passed through the pleura. In some embodiments, the initial location of the coaxial needle includes the coagulating agent discharge port residing within the pleura.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

As used herein, "biocompatible" means bioabsorbable, biodegradable, or resorbable.

The present invention includes a multistage bioabsorbable plug system and method of use. The system is comprised of a coagulating agent and an expandable plug. In some embodiments, the coagulating agent is an aqueous solution and the expandable plug is comprised of a non-liquid or non-fluid material, but may be configured to absorb an aqueous solution. In other words, the coagulating agent is fluidic in nature with an ability to flow as a fluid and no fixed shape prior to coagulation. In contrast, the expandable plug has a definable shape and while some embodiments can absorb fluids, the plug itself has a gel-like, semisolid, or solid state.

Some embodiments of the method include initially delivering the coagulating agent within an internal area of an organ/bodily cavity proximate the opening in the organ/cavity. A surgical procedure can then be performed and upon completion of the procedure, the expandable plug is inserted into the body adjacent to or within the opening in the organ, and the surgical instrument is removed. The combination of the coagulating agent and the plug seals the organ, thereby preventing the escape of bodily fluids.

Figure 1:
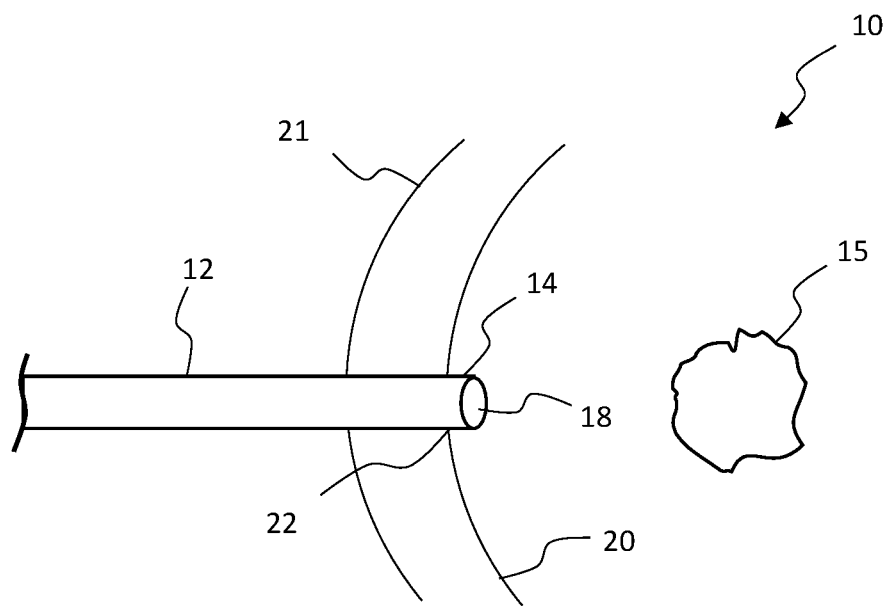
FIG. 1 is a diagram of a coaxial needle having penetrated a patient's skin and pleura.

Referring to FIG. 1, it will there be seen that the reference numeral 10 denotes a biopsy site as a whole. Openings in a mammalian body may be formed by numerous other medical procedures and non-medical events as mentioned earlier. However, a biopsy procedure is explained for exemplary purposes. Furthermore, while the exemplary biopsy site is located within a patient's lung, it should be understood that the utility of this invention is not restricted to sealing openings formed in lungs by biopsy procedures. Rather, this invention may be used to seal openings formed by any means in organs, such as the heart, brain, liver, spinal cord, and kidneys, and even in hard tissue such as bone, cartilage, and the like.

Figure 2:
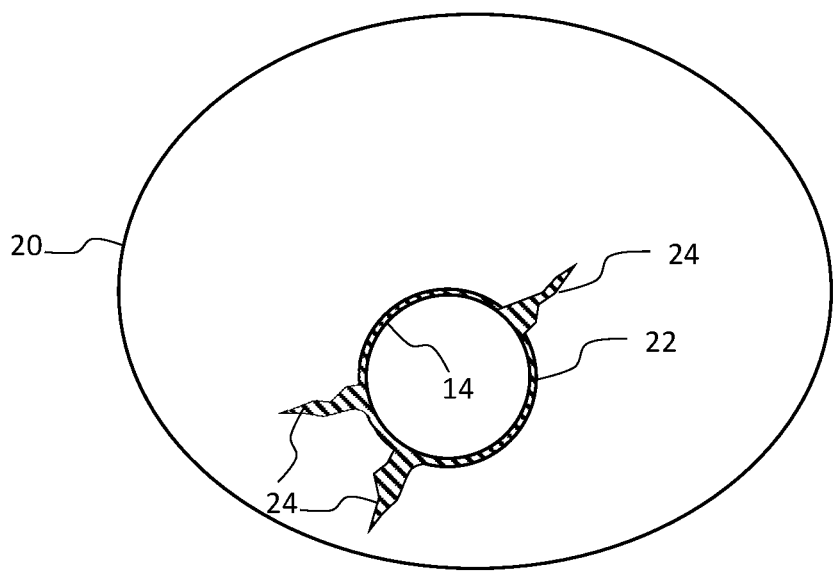
FIG. 2 is an illustration of radial tears resulting from inserting a coaxial needle through a section of a pleura.

As depicted in FIG. 1, a typical coaxial needle 12 is used to puncture patient's skin 21 and pleura 20 of the patient's lung. While the depicted passage 22 of coaxial needle 12 through pleura 20 of the patient's lung appears to be a clean circular hole generally equal to the outer diameter of coaxial needle 12, in practice, the hole is often accompanied by radial tears 24 in the tissue extending outwardly from needle passage 22 as depicted in FIG. 2. In such instances, the insertion of a plug in passage 22 is incapable of sealing these tears because the tears extend radially beyond the lateral expanse of the plug. Even the expanding hydrogel plug invented by the same inventors sometimes proved unable to seal these types of tears because the tears often extended radially beyond the lateral expanse of the hydrated plug. In addition, the delay in expansion of the plug sometimes resulted in the substantial pneumothorax, which in turn resulted in the lung collapsing.

Figure 3:
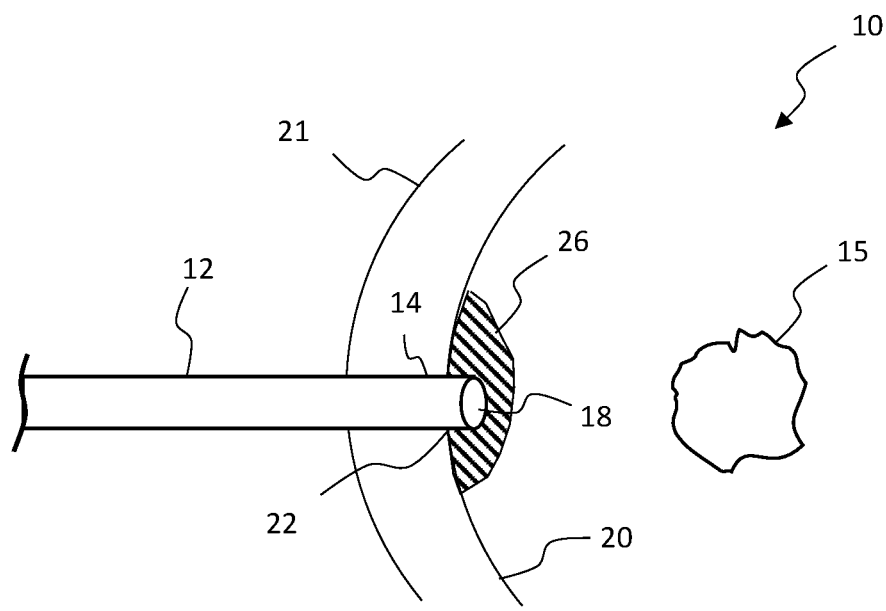
FIG. 3 is a diagram illustrating a step of inserting coagulating agent within a pleura after the coaxial needle has penetrated a patient's skin and pleura.

As best depicted in FIG. 3, the present invention overcomes these issues by depositing coagulating agent 26 that surrounds passage 22 and any radially extending tears 24. The coagulating agent is then able to seal any radial tears 24 while a plug can be inserted into passage 22 upon completion of the surgical procedure.

In some embodiments, the coagulating agent is the patient's blood, which may have been retrieved prior to or during the surgical procedure. The patients' blood is highly advantageous as a peripheral sealant because it is safe to the patient with no risk of the patient having an allergic or adverse reaction to their own blood. In addition, since blood is 90% water and is located in close contact to the desiccated or partially desiccated plug, the blood will act as a source for the high concentration of water immediately abutting the desiccated hydrogel plug to move via osmosis into the desiccated plug and could enhance the speed at which the plug expands to more rapidly fill the void of the biopsy tract. As a result, the use of blood further reduces the sealing time of the multistage plug system in comparison with other coagulating agents.

In some embodiments, the coagulating agent is a blood clot derived from the patient. Moreover, the coagulating agent may be comprised of or include an adhesive or a coagulation catalyst. In some embodiments, the coagulating agent is any agent known to a person of ordinary skill in the art that is biocompatible and adapted to transition from a liquid to a gel-like, semisolid state, or solid state. Some examples include but are not limited hyaluronic acid, moisture sensitive curing hydrogel, two-part curing hydrogel, and adhesive.

In some embodiments, roughly 10 cc of coagulating agent is inserted on the inside and/or the outside of the pleura/tissue barrier. Some embodiments, however, may use 10 cc to 20 cc of coagulating agent inserted on the inside and/or the outside of the pleura/tissue barrier. Some embodiments use at least 10 cc of coagulating agent inserted on the inside and/or the outside of the pleura/tissue barrier. In some embodiments, the volume of coagulating agent is dependent on the diameter of the coaxial needle.

Figure 4:
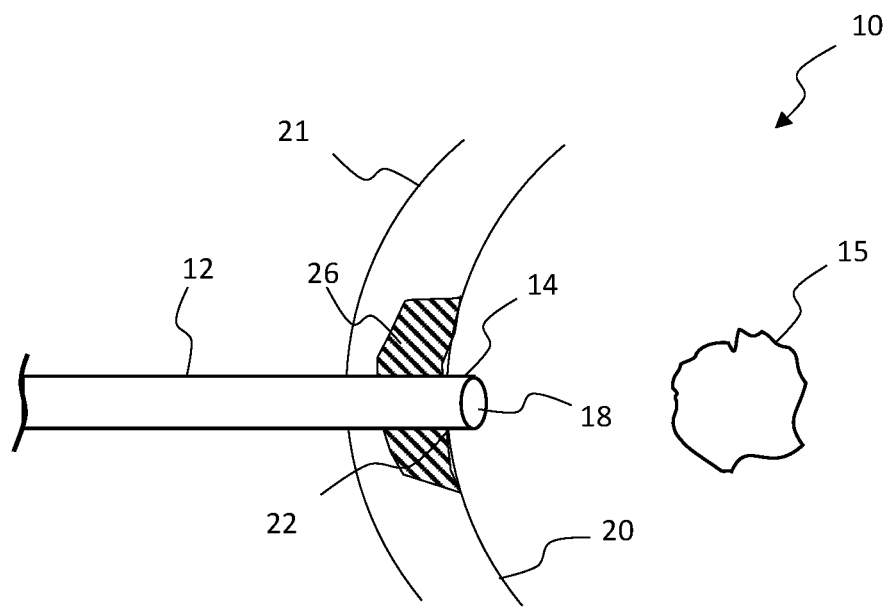
FIG. 4 is a diagram illustrating a step of inserting coagulating agent outside of a pleura after the coaxial needle has penetrated a patient's skin and pleura.
Figure 5:
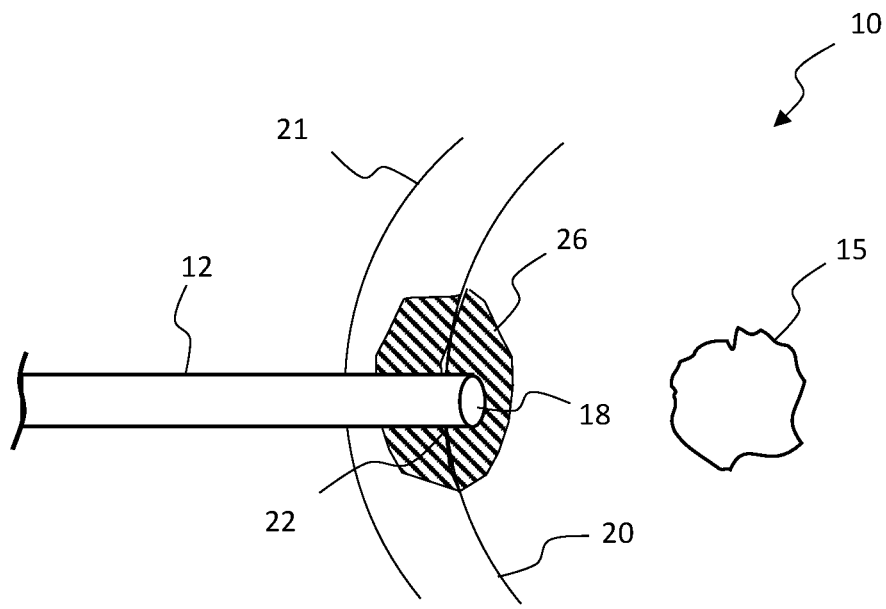
FIG. 5 is a diagram illustrating a step of inserting coagulating agent within and outside of a pleura.

In some embodiments, coagulating agent 26 is inserted proximate to the internal surface of pleura 20 as shown in FIG. 3. In some embodiments, coagulating agent 26 is inserted proximate to the external surface of pleura 20 as shown in FIG. 4. As shown in FIG. 5, some embodiments include inserting coagulating agent 26 proximate to both the internal and external surfaces of pleura 20.

To ensure that the coagulating agent is deposited sufficiently proximate to the surfaces of pleura 20, a coagulating agent discharge port is located within roughly 2 cm from the surface of the pleura. In some embodiments, the coagulating agent discharge port is located within roughly 1 cm from the surface of the pleura.

In some embodiments, the coagulating agent is initially deposited upon insertion of coaxial needle 12 through pleura 20. When the coagulating agent is initially deposited upon insertion of coaxial needle 12 through pleura 20, the coagulating agent has additional time to coagulate and can even seal or partially seal any radial tears 24 prior to the completion of the surgical procedure.

However, some embodiments include the coagulating agent being deposited just before or just after the plug is deposited within passage 22. The plug is typically deposited after sufficient biopsy samples have been retrieved and the biopsy needle has been removed from the coaxial needle. Thus, some embodiments include the coagulating agent being deposited after the biopsy samples have been retrieved, but before the coaxial needle is removed from the patient.

Figure 6:
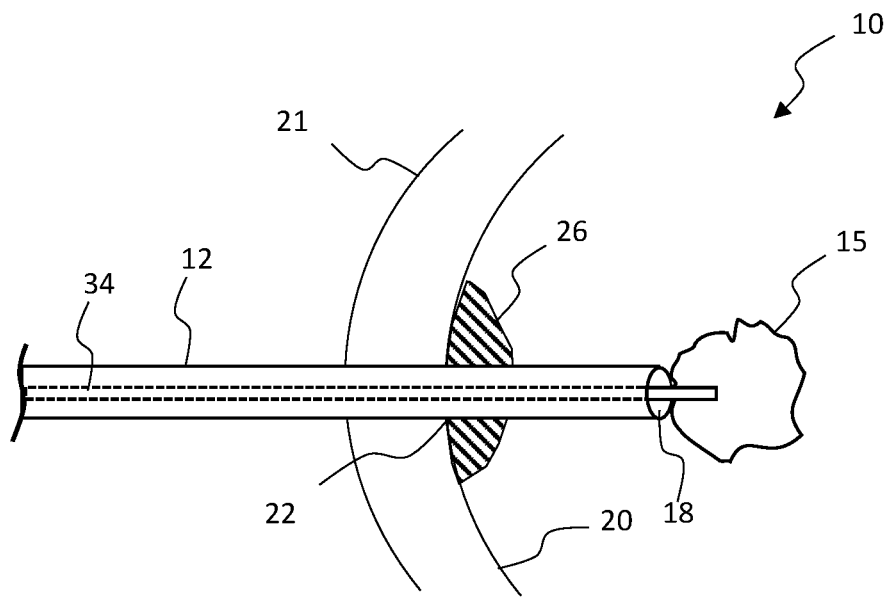
FIG. 6 is a diagram illustrating a step of advancing the coaxial needle to a surgical depth proximate to the tissue to be sampled.

FIG. 6 depicts the advancement of coaxial needle 12 to an adjacent location to tissue 15. Once coaxial needle 12 is moved to this surgical depth, biopsy needle 34 can retrieve tissue samples from tissue 15.

Figure 7:
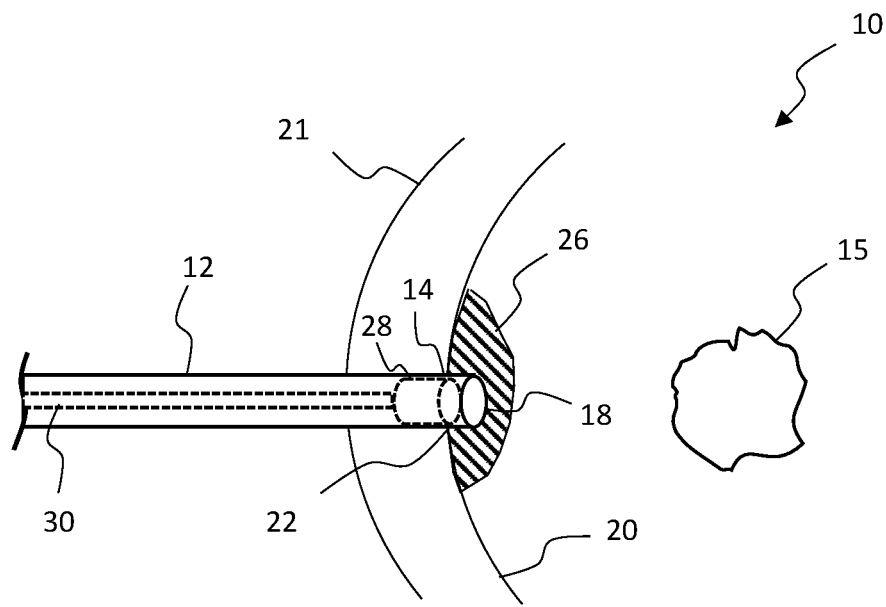
FIG. 7 is a diagram illustrating a step of inserting a plug within a pleura.
Figure 8:
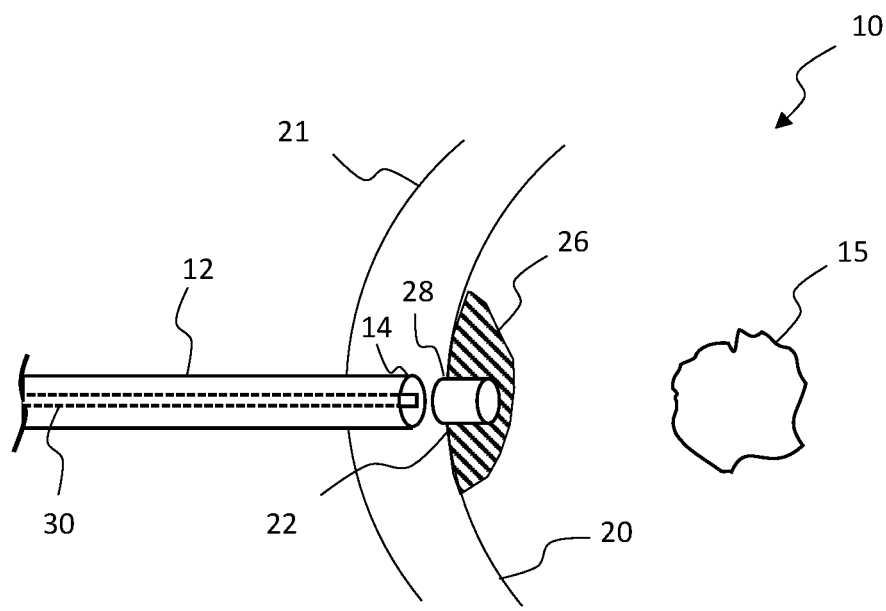
FIG. 8 is a diagram showing the plug just after the coaxial needle has been retracted from the pleura.

As shown in FIGS. 7-8, after the biopsy samples have been retrieved, but before the coaxial needle 12 has been completely removed from the pleura, plug 28 is inserted into passage 22. Plug 28 is formed of a material that expands upon contact with a stimulant such as water, blood, air, visible light, or other electromagnetic radiation such as a laser beam, a preselected chemical, and so on. In a preferred embodiment, the stimulant is moisture which is naturally present on the surface of a patient's lungs or other soft tissue, internal organs, or the like.

Thus, some embodiments of plug 28 have a dehydrated or partially dehydrated state and a hydrated state. Plug 28 is preferably configured to expand and seal passage 22 almost immediately to prevent unnecessary fluid loss through passage 22. While coagulating agent 26 may eventually seal passage 22, plug 28 helps expedite the process to account for delays in coagulation time. Essentially, plug 28 removes the coagulation time from consideration and allows a surgeon to almost immediately seal passage 22 regardless of how much time is required for coagulation agent to coagulate.

Depicted plug 28 is generally a solid cylindrical shape to easily pass through coaxial needle 12. In addition, plug 28 has a sufficient length to extend both inside and outside of pleura 20. In some embodiments, plug 28 has an elongated body that is not necessarily cylindrical. Moreover, plug 28 may have any cross-sectional shape, but preferably has a length sufficient to extend both inside and outside of pleura 20.

In some embodiments, plug 28 is roughly 2.5 cm in length in a dehydrated state and roughly 2 cm remains within pleura 20 and roughly 0.5 cm remains external to pleura 20 when plug 28 is in its inserted location. In some embodiments, plug 28 is roughly 3 cm in length in a dehydrated state and roughly 2 cm remains within pleura 20 and roughly 1 cm remains external to pleura 20 when plug 28 is in its inserted location. In some embodiments, the inserted location includes at least 0.5 cm extending internally or externally with respect to pleura 20.

In a dehydrated state, plug 28 has a cross-sectional area sufficient to allow plug 28 to pass through a lumen in coaxial needle 12. The hydrated state includes plug 28 having an expanded cross-sectional area that is greater than the cross-sectional area of coaxial needle 12 and passage 22. Plug 28 further includes various cross-sectional sizes during expansion that are larger than the cross-sectional size when dehydrated and smaller than the cross-sectional size when fully hydrated.

Plug 28 may be discharged from lumen 18 using pusher rod 30 as coaxial needle 12 is retracted out of pleura 20. This action is illustrated in comparing FIGS. 7 and 8. In some embodiments, the inserted location of plug 28 includes part of plug 28 remaining within pleura 20 and part of plug 28 located outside of pleura 20.

Figure 9:
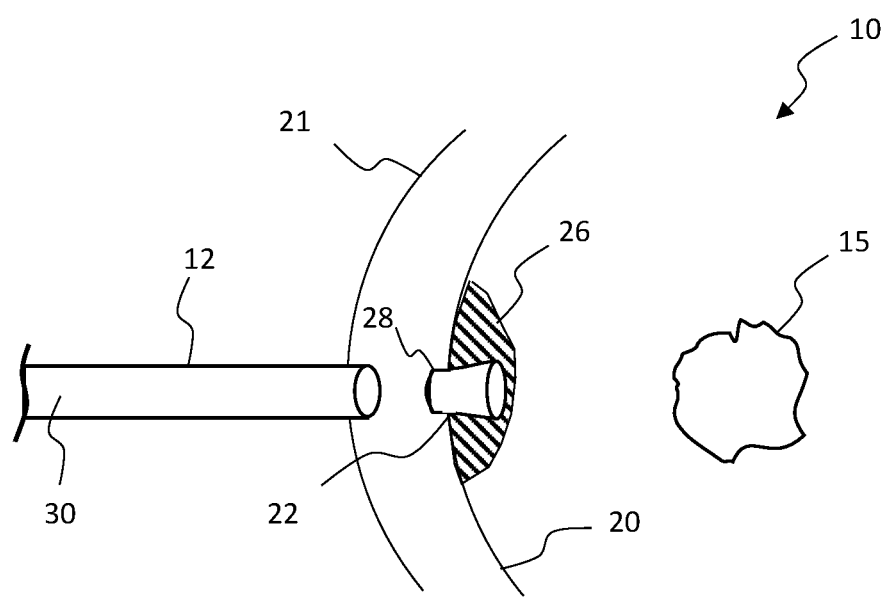
FIG. 9 is a diagram showing the plug during expansion after the coaxial needle has been retracted from the pleura.

As shown in FIGS. 8 and 9, plug 28 is expands when contacted by aqueous fluids, such as biological fluids or coagulating agent 26. FIG. 9 depicts plug 28 shortly after implantation and after having been in contact with moisture, or another predetermined stimulant, such that plug 28 has at least partially expanded. The expansion effectively seals the peripheral edge of the puncture opening and prevents air from escaping the lungs. In other applications, the plug is used to stop bleeding or other liquid fluid flow from the liver, heart, thecal sac, etc.

Plug 28 is also biocompatible, i.e., it is formed of a bioabsorbable material so that it is bioabsorbed by the body as the opening heals. Since people heal at different rates, a bioabsorbable material should be selected so that it is fully bioabsorbed in a period of time such as a few days to a few months.

Plug 28 may be comprised of any suitable bioabsorbable materials that expand when contacted by aqueous fluids including, but not limited to hydrogels, collagen, polysalactic acid, and any other suitable hydrophilic agents. Additional compositions include polymers that swell in the presence of aqueous fluids. Virtually all of the following polymers are hydrogels. Synthetic hydrogels can be prepared from the following classes of polymers and these are generally considered to be non-biodegradable: poly(hydroxyalkyl methylacrylates), such as poly(glyceryl methacrylate), poly(acrylamide), and poly(methacrylamide) and derivatives, poly(N-vinyl-2-pyrrolidone) anionic and cationic hydrogelspoly(vinylalcohol)poly(ethylene glycol) diacrylate and derivatives from block copolymers composed of poly(ethylene oxide)-poly(propyleneoxide)-poly(ethyleneoxide) and poly(propyleneoxide)-poly(ethyleneoxide)-poly(propyleneoxide) blocks, respectively.

Biodegradable synthetic hydrogels can be prepared from polymers such as those listed above by incorporating one or more of the following monomers: glycolide, lactide, E-caprolactone, P-dioxanone, and trimethylene carbonate. In addition, biodegradable hydrogels can be based on natural products such as polypeptides such as gelatin which may be cross-linked with formaldehyde or glutaraldehyde and various other dialdehydes.

Some other optional compositions include modified chitin hydrogels, which may be prepared from partially N-deacetylated chitin and then cross-linked with agents such as glutaraldehyde; dextran, a polysaccharide, derivatized with groups such as 3-acryloyl-2-hydroxypropyl esters and subsequently cross-linked by free radical copolymerization with N',N'-methylenebisacrylamide; starch that is similarly derivatized; and glycidyl acrylate followed by free radical cross-linking as described above.

Figure 10:
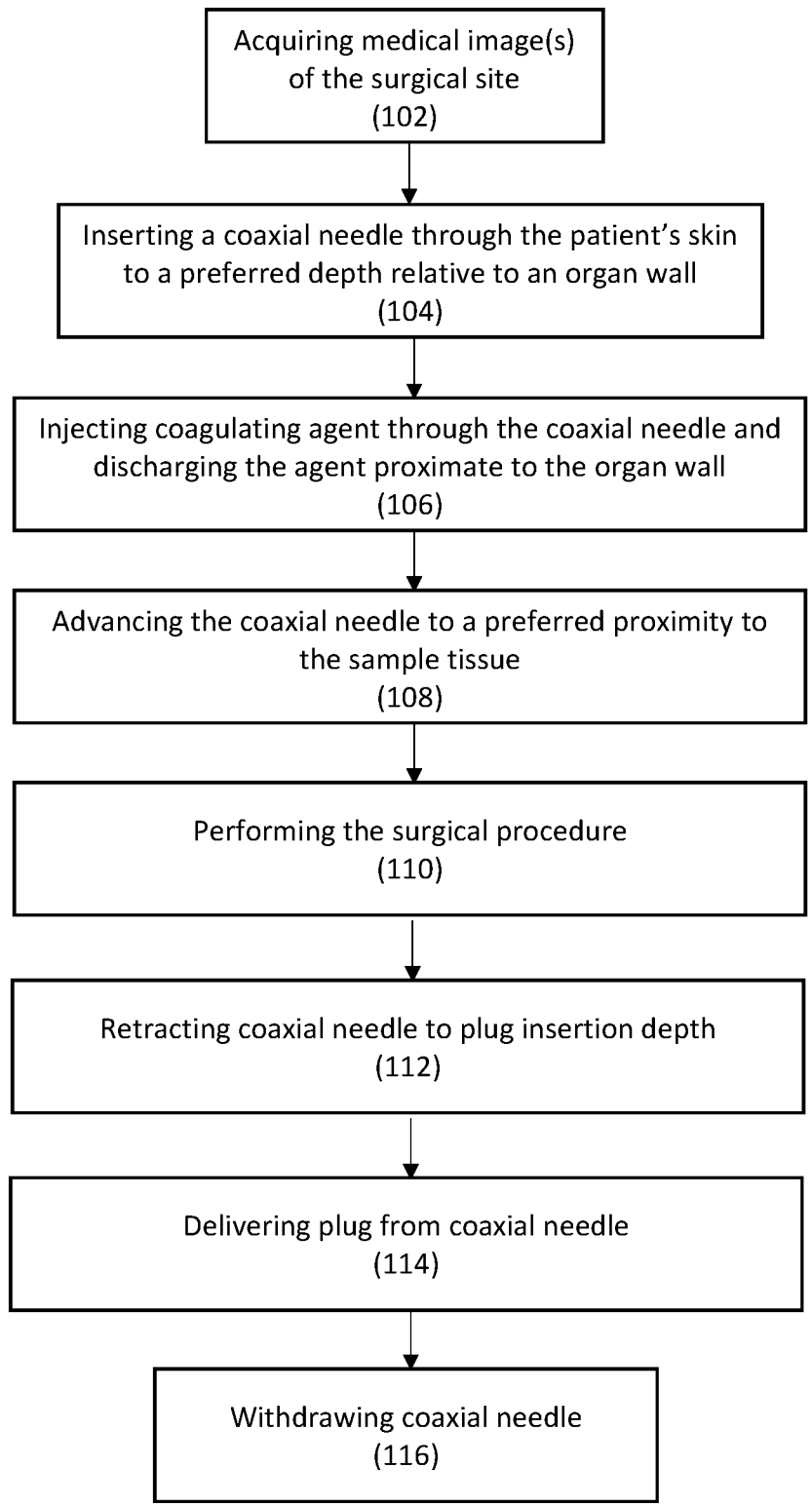
FIG. 10 is an exemplary flowchart of an embodiment of the present invention.

An embodiment of the novel method of the present invention is exemplified in FIG. 10 and corresponds to the illustrations in FIGS. 3-9. As previously noted, while the examples provided herein pertain to a lung biopsy procedure, the method can be performed for other surgical procedures that involve the puncturing of other bodily structures and/or organs.

Some embodiments include a first step 102 of acquiring one or more medical images of the surgical site. The medical images may be acquired by any imaging devices, including, but not limited to fluoroscopy, ultrasound, X-ray, magnetic resonance imaging, computed axial tomography (CAT) scanning, and other imaging techniques.

The images can be used to determine the distance between the patient's skin and the wall of the organ (the pleura in the case of a lung biopsy). That distance is then used in step 104 to guide the coaxial needle to an initial location in which the distal end of the coaxial needle is within a preferred distance from the wall of the organ. In some embodiments, the preferred depth includes the distal end of the coaxial needle being roughly 2 cm within the organ. In some embodiments, the distal end of the coaxial needle is between roughly 1 cm and 2 cm from the wall of the organ.

Figure 11:
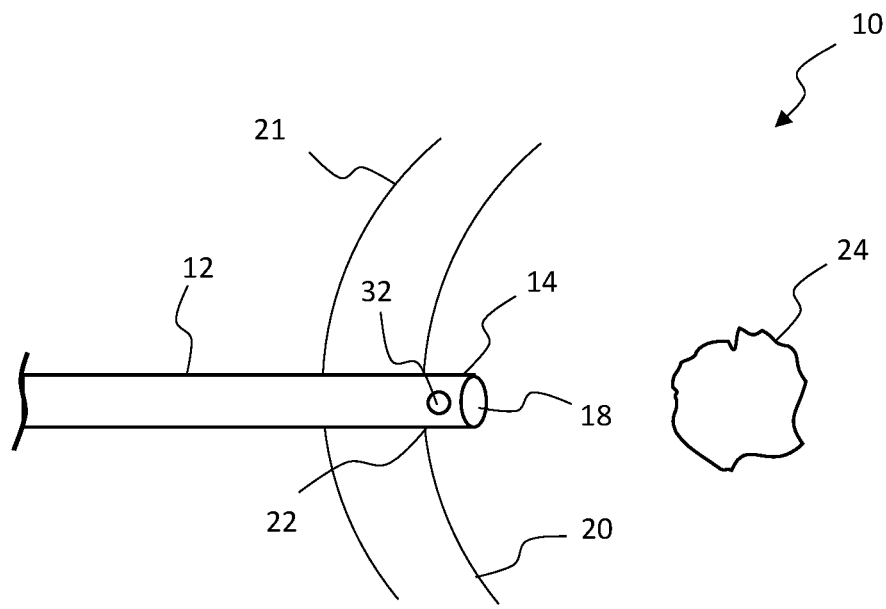
FIG. 11 is a diagram of a coaxial needle having a laterally disposed coagulating agent discharge port after the coaxial needle has penetrated a patient's skin and pleura.
Figure 12:
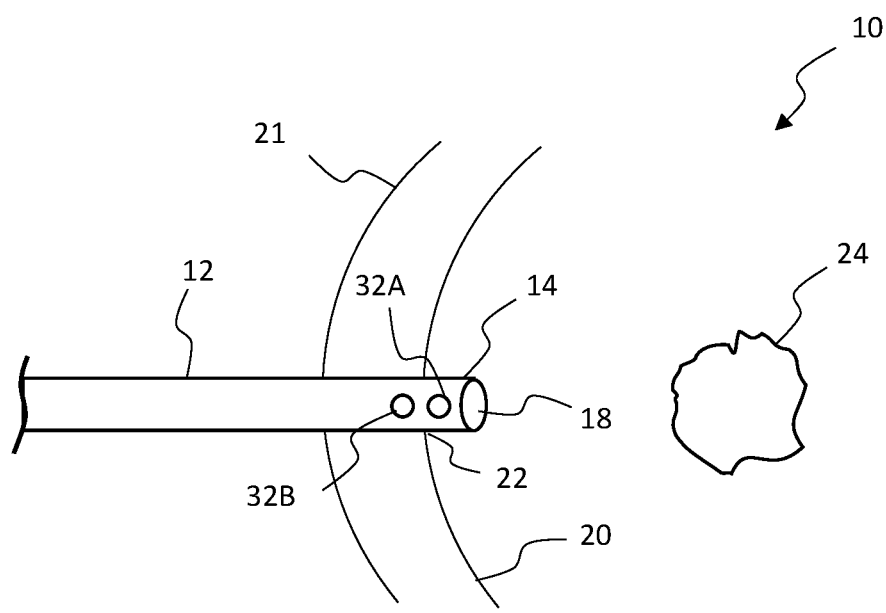
FIG. 12 is a diagram of a coaxial needle having a multiple laterally disposed coagulating agent discharge ports after the coaxial needle has penetrated a patient's skin and pleura.
Figure 13:
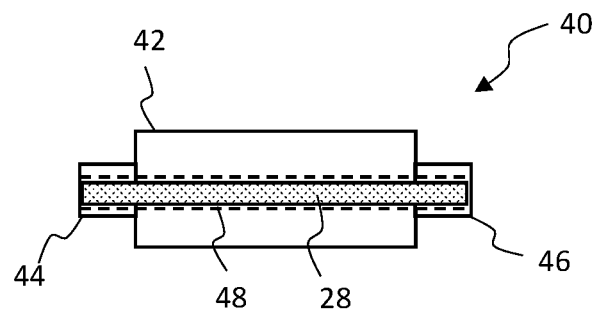
FIG. 13 is an embodiment of a plug delivery housing.

Some embodiments, however, include coaxial needle 12 having one or more coagulating agent discharge ports 32 located in the lateral wall of coaxial needle 12 as shown in FIGS. 11 and 12. In such instances, the preferred depth of coaxial needle 12 includes discharge ports 32 located within roughly 2 cm from organ wall 20. In some embodiments, the preferred depth of coaxial needle 12 includes discharge ports 32 located between roughly 1 cm and 2 cm from organ wall 20.

As shown in FIG. 12, some embodiments include multiple coagulating agent discharge ports 32A and 32B located in the lateral wall of coaxial needle 12. Again, the preferred depth of discharge ports 32A and 32B is roughly 2 cm from organ wall 20. In some embodiments, the preferred depth of coaxial needle 12 includes discharge ports 32A and 32B located between roughly 1 cm and 2 cm from organ wall 20.

Some embodiments of the coaxial needle that include laterally disposed discharge ports also include a seal or membrane distally located from the discharge ports. The membrane is configured to seal the aperture in the distal end of the coaxial needle to ensure that the coagulating agent exits the discharge ports rather than the aperture in the distal end of the coaxial needle. The membrane is further configured to open in response to an actuator or in response to a needle or other surgical instrument applying a force to the internal/proximal surface of the membrane.

Some embodiments of the membrane include a plurality of triangular shaped flaps with the vertices of the triangles meeting generally in the middle of the membrane. A needle can be forced through the meeting point of the vertices and the triangular sections of the membrane give way to the advancing needle. In some embodiments, the flaps are of a different shape so long as they collectively act to seal the lumen of the coaxial needle. In some embodiments, the flaps are made of a flexible material. In addition, the flaps are preferably in overlapping or in a sealable relationship with each other when not subject to the external force of a needle or surgical instrument.

Referring back to FIG. 10, at step 106, once coaxial needle 12 reaches its initial insertion depth, coagulating agent 26 is forced through the internal lumen 18 of coaxial needle 12 and deposited proximate to passage 22 as shown in FIGS. 3-5. Some embodiments include injecting coagulating agent through coaxial needle 12 via primary lumen 18 or through one or more secondary lumens connected to discharge port(s) 32. The coagulating agent is delivered proximate to the organ wall based on the type of coaxial needle in use and the preferred initial location of the discharge ports/distal end of the coaxial needle.

The amount and composition of the coagulating agent used in the novel method may be any of those described herein. In addition, the location of the coagulating agent may be in line with those described herein. Likewise, the plug used in the novel method may be any size, shape and composition disclosed herein.

After the coagulating agent has been injected, at step 108, coaxial needle 12 is further advanced into the patient to bring distal end 14 of coaxial needle 12 into contact with or within a preferred proximity to the tissue intended to be sampled (referred to hereinafter as "sample tissue 15") as shown in FIG. 6. The surgical procedure, such as a tissue biopsy, is then performed at step 110. When a sufficient amount of biopsy samples has been retrieved, the biopsy needle is withdrawn from coaxial needle 14. Then, at step 112, coaxial needle 12 is retracted to a plug insertion depth and held at this location while plug 28 is inserted and moved to distal end 14.

The plug insertion depth is illustrated in FIG. 7. In some embodiments, the plug insertion depth of coaxial needle 12, includes distal end 14 roughly 2 cm within pleura 20. In some embodiments, the plug insertion depth includes distal end 14 between roughly 0.5 cm and 2.5 cm within pleura 20. Preferably the plug insertion depth includes distal end 14 being a predetermined distance from pleura 20 that is equal to or less than the length of plug 28 to ensure that plug 28 resides at least partially within passage 22 in pleura 20.

Once coaxial needle 12 is located at the plug insertion depth, plug 28 is discharged from coaxial needle 12 at step 114 to deliver plug 28 within or adjacent to passage 22. In some embodiments, as depicted in FIGS. 7-8, pusher rod 30 is used to force plug 28 from lumen 18 in coaxial needle 12. Specifically, pusher rod 30 is held in place when coaxial needle 12 is withdrawn to ensure that plug 28 does not move. Plug 28 may be delivered by any suitable pushing means or installed by any other suitable method. The particular method of installation may depend upon the type of opening being plugged.

After plug 28 has been delivered, coaxial needle 12 is withdrawn from the patient at step 116, the action of which is exemplified in FIGS. 8-9. The stimulus then causes expansion of the plug and sealing of the opening made by the needle.

Some embodiments include a step of inserting the coagulating agent after the plug has been delivered. Some embodiments include inserting coagulating agent before and after the plug is delivered. In some embodiments, the coaxial needle has one or more side ports and lateral discharge ports such that the plug and coagulating agent can be delivered simultaneously.

In some embodiments, the plug is pre-hydrated prior to insertion into the patient. The pre-hydration reduces the time necessary for the plug to reach its maximum expansion. In some embodiments, the plug is pre-hydrated to 25% of its maximum expansion. In some embodiments, the plug is pre-hydrated to between 10% and 30% of its maximum expansion. In some embodiments the plug is pre-hydrated for roughly 5 minutes. In some embodiments the plug is pre-hydrated for roughly 3 minutes to 10 minutes.

The pre-hydration step may be accomplished using one or more plug delivery housings 40, such as those exemplified in FIGS. 13-16. Plug delivery housing 40 includes main body 42 with proximal connector 44 and distal connector 46. Bore 48 extends longitudinally through main body 42 and connectors 44 and 46. Bore 48 is sized to receive and temporarily house plug 28 in a dehydrated or partially hydrated state. In some embodiments, one or both of connectors 44 and 46 include threads to engage a complementary thread on an insertion instrument, such as an insertion needle.

Figure 14:
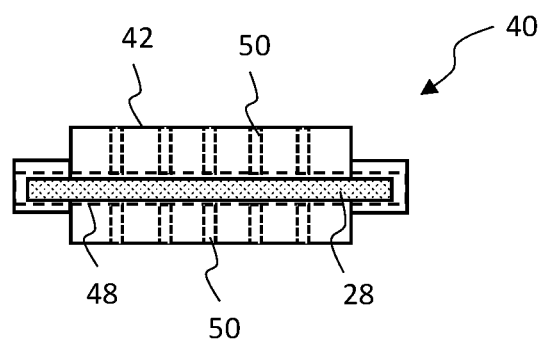
FIG. 14 is an embodiment of a plug delivery housing.
Figure 16:
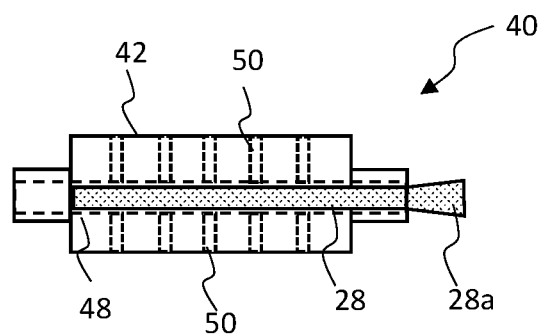
FIG. 16 is an embodiment of a plug delivery housing.

During the pre-hydration step, plug delivery housing 40, with an already inserted plug 28, is deposited into an aqueous solution or brought into contact with an aqueous solution to allow plug 28 to begin pre-hydrating. As best shown in FIGS. 14 and 16, some embodiments of plug delivery housing 40 include one or more hydration channels 50. Hydration channels 50 extend generally in a lateral direction and provide a fluidic passageway to deliver aqueous solution to bore 48 and in turn plug 28 to allow for quicker and more consistent pre-hydration of plug 28.

Figure 15:
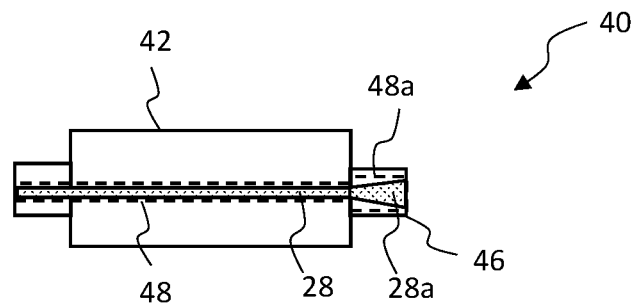
FIG. 15 is an embodiment of a plug delivery housing.

As shown in FIG. 15, some embodiments of plug delivery housing 40 include distal connector 46 having a cavity or a distal portion 48a of bore 48 having a larger diameter than the other proximal sections of bore 48. As a result, distal section 28a of plug 28 is able to hydrate and expand to a larger extent than the remaining sections of plug 28. As a result, distal section 28a is less likely to accidentally pass through passage 22 when coaxial needle 12 is removed. Essentially, distal section 28a acts an expanded anchor.

As shown in FIG. 16, the same result can be achieved by extending distal section 28a outside of bore 48 prior to pre-hydrating plug 28. Again, distal section 28a of plug 28 is able to hydrate and expand to a greater size than the remaining sections of plug 28. As a result, distal section 28a acts an expanded anchor to reduce the likelihood of distal section 28a accidentally passing through passage 22 when coaxial needle 12 is removed.

Accordingly, in some embodiments, the pre-hydration step includes positioning distal section 28a of plug 28 in cavity 48a or distally outside of bore 48 prior to plug 28 contacting an aqueous solution. Moreover, it should be noted that while FIGS. 13-16 show different embodiments with different features, embodiments of plug delivery housing 40 may include any combination of the depicted features.

Some embodiments of the novel method of the present invention further include a step of extracting a patient's blood and then using the extracted blood as the coagulating agent. In some embodiments, the blood is modified. For example, additional adhesives or coagulation catalysts may be added to the patient's blood.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of sealing a pleura in a patient, comprising:
   determining a distance between a patient's skin and the pleura;
   inserting a coaxial needle through the patient's skin, wherein the coaxial needle has a coagulating agent discharge port through which a coagulating agent can be discharged into the patient;
   bringing the coaxial needle to an initial location in which the coagulating agent discharge port is 2 cm or less in distance from the pleura;
   while the coaxial needle is at the initial location, injecting coagulating agent into the patient via the coaxial needle, such that the coagulating agent exits the coagulating agent discharge port, wherein the coagulating agent is comprised of blood;
   after injecting the coagulating agent, advancing the coaxial needle to a surgical location and performing a surgical procedure;
   following the surgical procedure, retracting the coaxial needle to a plug discharging depth, wherein the plug discharging depth includes a plug discharge port within 2 cm from an internal surface of the pleura;
   discharging a plug from the plug discharge port while retracting the coaxial needle, such that the plug resides at least partially within the pleura, wherein the plug is comprised of a biocompatible hydrogel configured to expand upon contact with an aqueous fluid; and
   withdrawing the coaxial needle from the patient.

2. The method of claim 1, further including pre-hydrating the plug prior to discharging the plug from the plug discharge port.

3. The method of claim 1, wherein the plug is inserted into the coaxial needle in a dehydrated state.

4. The method of claim 1, further including retrieving blood from the patient and using the blood as the coagulating agent.

5. The method of claim 1, wherein the coagulating agent is 10 cc of blood.

6. The method of claim 1, wherein the initial location of the coaxial needle includes a portion of the coaxial needle having passed through the pleura.

7. The method of claim 1, wherein the initial location of the coaxial needle includes the coagulating agent discharge port residing within the pleura.

8. The method of claim 1, further including injecting the coagulating agent when the coaxial needle is at the plug discharging depth.

9. The method of claim 1, wherein the plug is configured to absorb the coagulating agent.

10. A method of sealing a pleura in a patient, comprising:
    determining a distance between a patient's skin and the pleura;
    inserting a coaxial needle through the patient's skin and the pleura, wherein the coaxial needle has a coagulating agent discharge port through which a coagulating agent can be discharged into the patient;
    bringing the coaxial needle to an initial location in which the coagulating agent discharge port resides within the pleura;
    while the coaxial needle is at the initial location, injecting coagulating agent into the patient via the coaxial needle, such that the coagulating agent exits the coagulating agent discharge port and is delivered within the pleura;
    after injecting the coagulating agent, advancing the coaxial needle to a surgical location and performing a surgical procedure;
    following the surgical procedure, retracting the coaxial needle to a plug discharging depth, wherein the plug discharging depth includes a plug discharge port within 2 cm from an internal surface of the pleura;
    discharging a plug from the plug discharge port while retracting the coaxial needle, such that the plug resides at least partially within the pleura, wherein the plug is comprised of a biocompatible hydrogel configured to expand upon contact with an aqueous fluid; and
    withdrawing the coaxial needle from the patient.

11. The method of claim 10, further including pre-hydrating the plug prior to discharging the plug from the plug discharge port.

12. The method of claim 10, wherein the plug is inserted into the coaxial needle in a dehydrated state.

13. The method of claim 10, further including retrieving blood from the patient and using the blood as the coagulating agent.

14. The method of claim 10, wherein the coagulating agent is 10 cc of blood.

15. The method of claim 10, further including injecting the coagulating agent when the coaxial needle is at the plug discharging depth.

16. The method of claim 10, wherein the plug is configured to absorb the coagulating agent.

* * * * *